US009192343B2

(12) United States Patent
Eklund

(10) Patent No.: US 9,192,343 B2
(45) Date of Patent: Nov. 24, 2015

(54) FLUOROSCOPY SYSTEM

(71) Applicant: Scanflex Healthcare AB, Stockholm (SE)

(72) Inventor: Markus Eklund, Sundbyberg (SE)

(73) Assignee: SCANFLEX HEALTHCARE AB (SE)

(*) Notice: Subject to any disclaimer, the term of this patent is extended or adjusted under 35 U.S.C. 154(b) by 0 days.

(21) Appl. No.: 14/083,469

(22) Filed: Nov. 19, 2013

(65) Prior Publication Data
US 2015/0139389 A1    May 21, 2015

(51) Int. Cl.
G01D 18/00    (2006.01)
G03B 42/02    (2006.01)
G21K 1/04     (2006.01)
A61B 6/06     (2006.01)
A61B 6/00     (2006.01)

(52) U.S. Cl.
CPC .. *A61B 6/06* (2013.01); *A61B 6/467* (2013.01)

(58) Field of Classification Search
CPC ........ A61B 6/06; A61B 6/542; A61B 6/4441; A61B 6/487; A61B 6/485; G21K 1/04; G01N 23/04; A61N 2005/1061
USPC .......................... 378/147, 4, 42, 62, 98.5, 102
See application file for complete search history.

(56) References Cited

U.S. PATENT DOCUMENTS

| 2003/0169847 | A1* | 9/2003 | Karellas et al. | 378/98.3 |
| 2013/0083894 | A1* | 4/2013 | Niebler et al. | 378/62 |
| 2013/0245429 | A1* | 9/2013 | Zhang et al. | 600/424 |
| 2014/0126696 | A1* | 5/2014 | Xu et al. | 378/62 |

FOREIGN PATENT DOCUMENTS

| EP | 2309863 A1 | 7/2013 |
| JP | 2003290198 A | 10/2003 |
| JP | 2006122448 A | 5/2006 |
| JP | 2009136425 A | 6/2009 |

OTHER PUBLICATIONS

Swemac "Imaging: Biplanar 500".

* cited by examiner

*Primary Examiner* — Nikita Wells

(57) ABSTRACT

A mobile digital fluoroscopy system comprises either a G-arm (18) stand (1) having two X-ray beam transmitter (21,23)/receiver (22,24) pairs arranged at right angles to each other or a C-arm having a single transmitter/receiver pair. Protective collimator shutter plates (1060) at each transmitter limit the X-ray irradiation area. These collimator plates are properly adjusted via servo motors prior to or during the operation, by fingertip movements, touching collimator representations on a touchscreen for each transmitter/receiver pair, to provide both protection to the surgeon and patient and sufficient fluoroscopic view to the surgeon of the operation site of interest in the body.

17 Claims, 12 Drawing Sheets

FLUOROSCOPY SYSTEM

FIELD OF THE INVENTION

The present invention relates in general to a preferably mobile digital fluoroscopy system for medical applications operating with an X-ray device mounted to generate X-ray images.

More specifically, the present invention relates to a fluoroscopy system having one or more X-ray devices each provided with a digital X-ray detector, and oriented on different axes to provide different views of the location of interest in the patient with the ability to narrow or widen the area of the patient exposed to the X-ray beam via a graphical user interface (GUI), such as a touch screen.

BACKGROUND

In orthopedic surgery environment, there is a need for allowing full access to the operating area with total control at each step. Therefore, X-ray imaging using C-stands or G-stands comprising imaging systems is commonly used, wherein a C-stand only has one X-ray imaging device while a so-called G-stand comprises two such imaging devices, with their axes oriented at an angle to each other.

A symmetrical G-stand may in some circumstances be preferable to a C-stand, since it comprises two perpendicularly mounted X-ray imaging devices, and is thereby able to provide both frontal and lateral X-ray imaging with fixed settings. The ability to simultaneously see the surgical area in both a frontal and lateral view reduces the need to move and adjust the equipment during surgery, thus reducing both surgery time and radiation dose. When the need to move the equipment is reduced, better sterility is also achieved.

X-ray imaging devices may be used for accurate positioning of implants thereby creating a safer and more reliable method of surgery. The X-ray devices are fixed in perpendicular relation to each other and may be tilted somewhat for better access and views.

A general problem in the technical field of X-ray imaging is to protect personnel involved in surgery as well as parts of the patient's body, not part of an area of interest, from unnecessary exposure to X-ray radiation. A common way to achieve this is that the X-ray beam is narrowed by protective lead collimator shutters.

A problem with conventional systems is to easily and accurately narrow or widen the X-ray beam, used for imaging, to the area of interest as the area of interest may change, e.g. during surgery. There is a need to improve the user's or surgeon's understanding of what the selected area of interest is and to improve the method of changing the area of interest during use of the X-ray imaging device, e.g. as surgery proceeds.

In presently used systems, keyed in numerical values are often used to adjust the physical positions of the collimators. This is very indirect, difficult and non-intuitive. These difficulties will result in non-optimal setting of the collimators, and most likely overexposure X-ray radiation.

RELATED ART

An example of such a mobile digital fluoroscopy system is described in patent application WO 03/077762.

One example of a G-stand X-ray system is shown and described in WO 96/11633 Further examples of related art are shown in the following publications:
US 2005/0116878 A1
U.S. Pat. No. 6,789,941
U.S. Pat. No. 7,231,014
U.S. Pat. No. 6,431,751
US2C212308A1
US2C213338A1
US20070255292
U.S. Pat. No. 7,403,591

SUMMARY OF THE INVENTION

The general object of the invention is to provide improvements in a digital fluoroscopy system for medical applications operating with first and optionally a second X-ray imaging device mounted on a C-stand or G-stand to generate X-ray images along two mutually intersecting axes.

A problem with conventional systems is to easily and accurately narrow or widen the x-ray beam, used for imaging prior to surgery in compliance with safety policies and regulations. The area of interest may change during surgery. There is a need to improve the user's or surgeon's understanding of what the selected area of interest is and to improve the method of changing the area of interest as surgery proceeds. There is also a need to facilitate rapid, accurate and intuitive setting of the protective collimators, to avoid overexposure to X-rays and to provide optimal viewing of the area of interest.

One embodiment of the invention effects this narrowing or widening of the irradiated area by the use of collimator plates disposed in front of a beam transmitter in each X-ray imaging device together with servo motors controlled by user input on a touchscreen, thereby narrowing the exposed area of the patient irradiated with X-rays and imaged on a display.

One embodiment of the invention effects this narrowing or widening of the irradiated area by the use of a dilatable collimator iris disposed in front of a beam transmitter in each X-ray imaging device together with servo motors controlled by user input on a touchscreen, thereby narrowing or widening the irradiated area of the patient and imaged on a display.

One embodiment of the invention solves this narrowing or widening the irradiated area by the use of a dilatable collimator iris and collimator plates disposed in front of a beam transmitter in each X-ray imaging device together with servo motors controlled by user input on a touchscreen, thereby narrowing or widening the irradiated area of the patient and imaged on a display.

In one embodiment of the invention a stored unnarrowed still image is shown on a touch screen and a user can narrow or widen the irradiated area via user touchscreen input data that is received by a control unit. The control unit is configured to process user input data to control data indicative of a desired servo motor position, to send said control data as control signals to a servo motor unit adapted to receive control data as control signals from said control unit, to control servo motors to a predetermined position based on said control data by sending servo motor signals, thereby causing the dilatable collimator iris or collimator plates to narrow or widen the irradiated area.

In one embodiment of the invention the actual current movement of the collimators in response to touchscreen input data is indicated on the touchscreen by obtaining in a servo motor unit servo motor status data indicative of the status of a servo motor, by sending servo motor status data as status control signals from said servo motor unit to said control unit, by receiving servo motor status data as status control signals by a control unit from a servo motor unit, processing servo motor status data to a visual representation of said servo motor status data and to send said visual representation to said touch screen as a display signal, wherein said touch screen is configured to display said visual representation to a user.

For safety reasons it is important that these collimator plates be adjusted properly and accurately before the operation.

One specific object of the present invention is to provide improvements in the apparatus for setting the protective collimators in a mobile digital fluoroscopy system. It has hitherto been difficult to see to it that the collimators are precisely and easily positioned prior to irradiation with X-rays.

Embodiments of the invention provide such improvements, as described herein.

The digital fluoroscopy system comprising a G-arm may also be referred to as a G-arm system, or a G-stand.

The digital fluoroscopy system comprising a C-arm may also be referred to as a C-arm system, or a C-stand.

The object is fulfilled and the problem is solved by embodiments of the invention as described below and in the accompanying claims.

Embodiments of the invention comprise a mobile C-arm or G-arm fluoroscopy system provided with digital X-ray detectors.

According to one embodiment, there is provided a mobile digital fluoroscopy system, comprising a mobile unit 1 having a stand having a G-arm 18 suspended on a chassis frame 7; a first X-ray device 19 mounted on the G-arm 18 to transmit an X-ray beam along a first axis P1, the first X-ray device 19 having a first receiver 22 mounted on the G-arm 18 and a first transmitter 21 mounted on the G-arm 18 opposite said first receiver 22; a second X-ray device 20 mounted on the G-arm 18 to transmit an X-ray beam along a second axis P2 intersecting the first axis P1 of the first X-ray device, the second X-ray device 20 having a second receiver 24 mounted on the G-arm 18 and a second transmitter 23 mounted on the arm 18 opposite said second receiver 24, wherein said first and second receivers 22 and 24 are flat digital X-ray detectors mounted at respective ends of the G-arm.

According to another embodiment of the invention, the mobile unit 1, has a stand with a so-called C-arm, with X-ray beams transmitted only along one axis P1 between a single transmitter and receiver pair.

BRIEF DESCRIPTION OF THE DRAWINGS

The present invention will be further explained below with reference to the accompanying drawings, in which:

FIG. 1-FIG. 8 show a schematic overview of one embodiment of the invention in a digital fluoroscopy system configured on a G-arm, wherein FIG. 1 shows a perspective view of the G-stand of the system as seen from a first direction.

FIG. 2 shows a perspective view as seen from a second direction.

FIG. 3 shows the G-stand of the system in a first side elevation.

FIG. 4 shows the G-stand of the system from a second side elevation.

FIG. 5 shows another form of G-stand used in a system according to the invention, showing a patient with her neck at the intersection of the two X-ray axes.

FIG. 6 shows one embodiment of a fluoroscope system comprising a mobile unit and a control console.

FIG. 7 shows a control console to be used in the system according to the invention.

DETAILED DESCRIPTION OF THE INVENTION

System Overview

The present invention concerns an X-ray apparatus configured as a system of components illustrated in FIG. 1 to FIG. 5, adapted for use in connection with surgical orthopedic operations.

Figure 1:
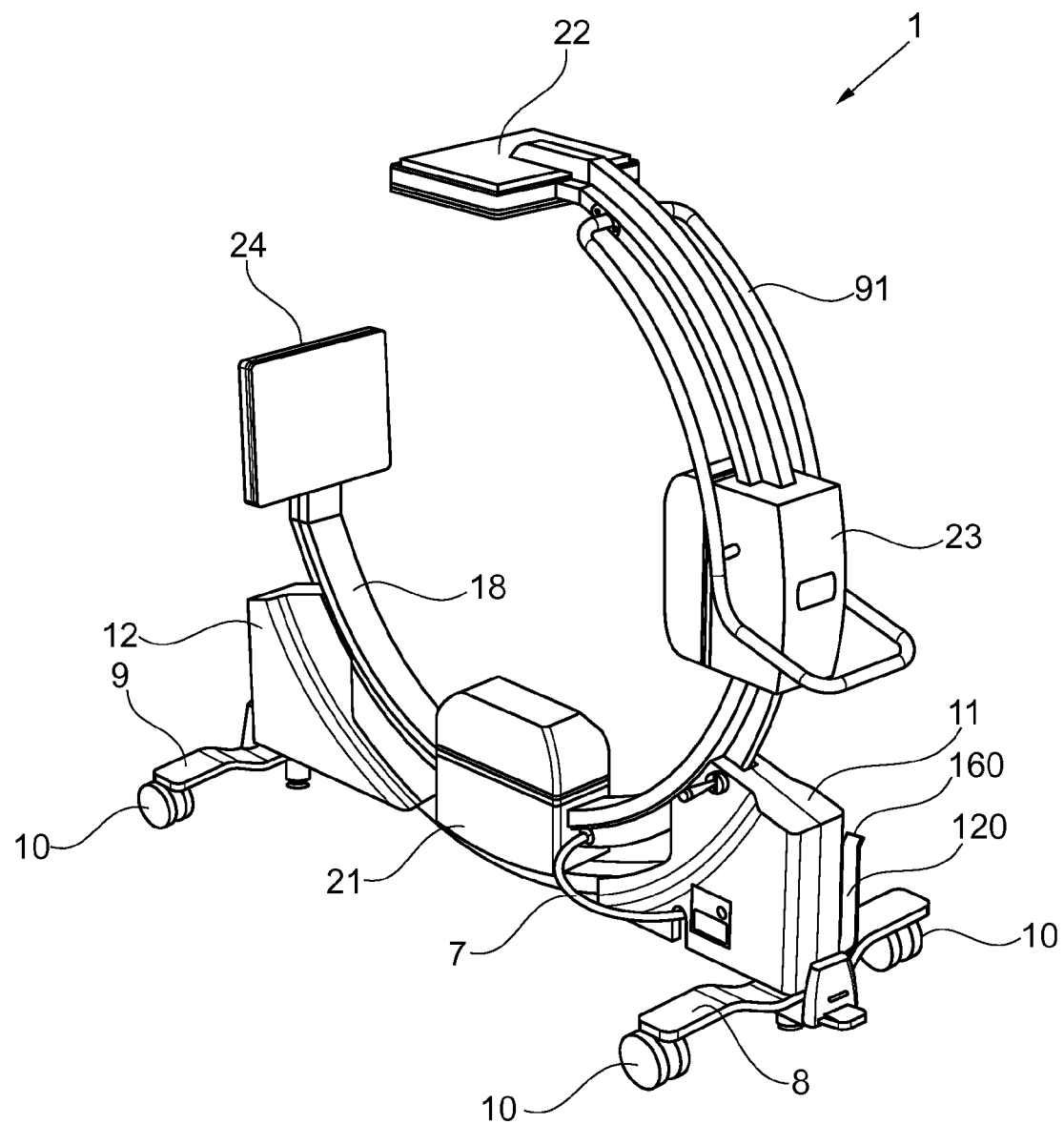
Figure 2:
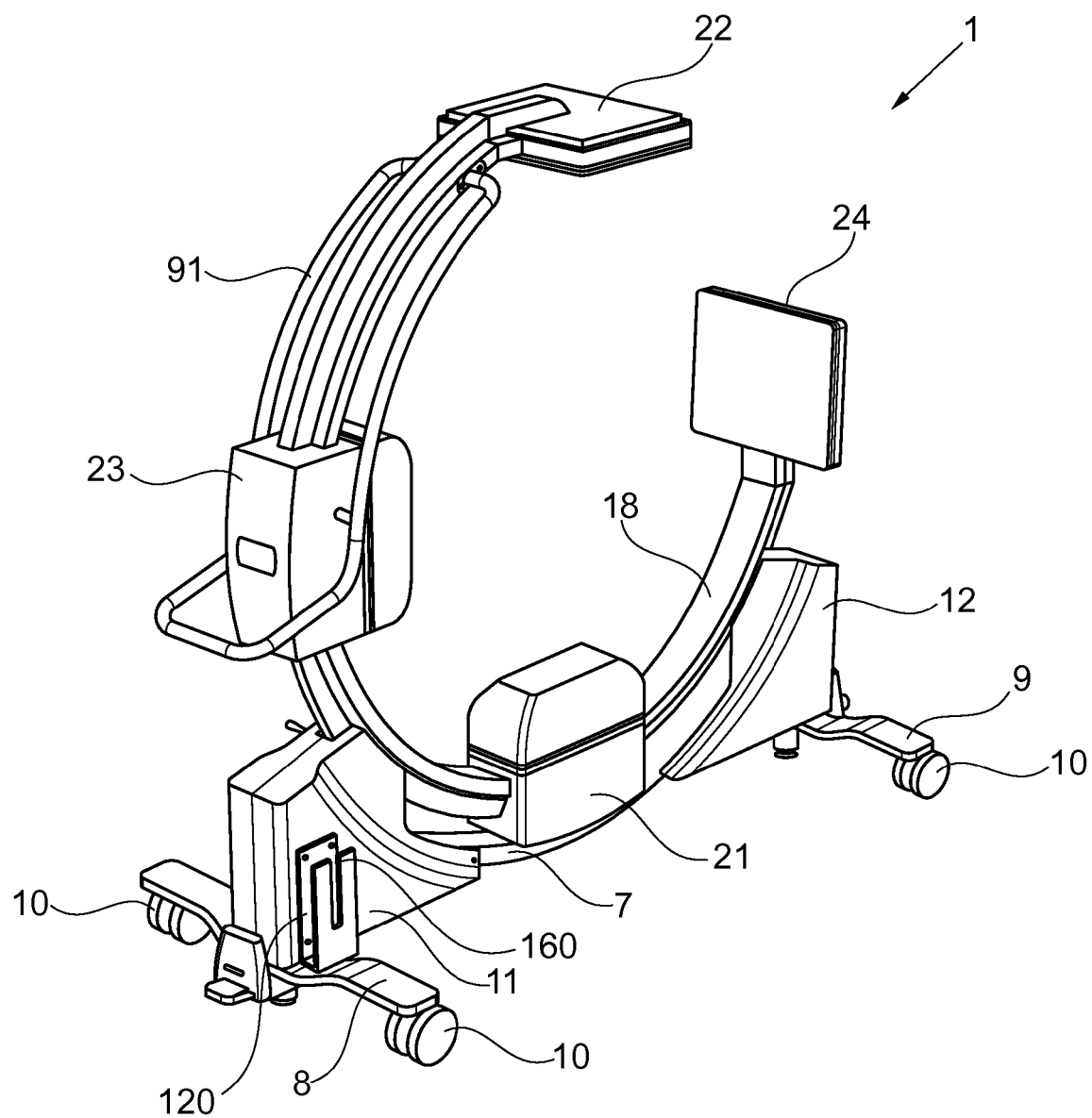
Figure 3:
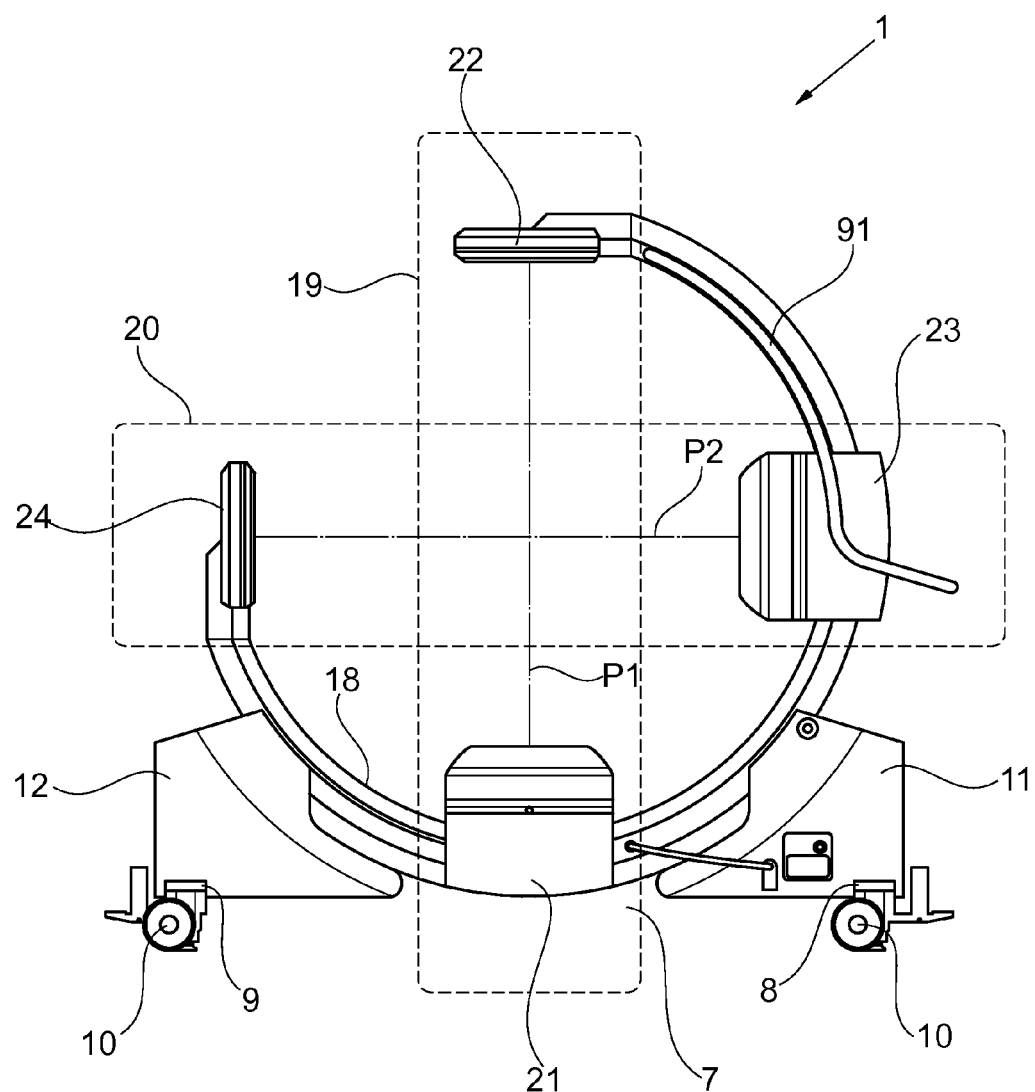
Figure 4:
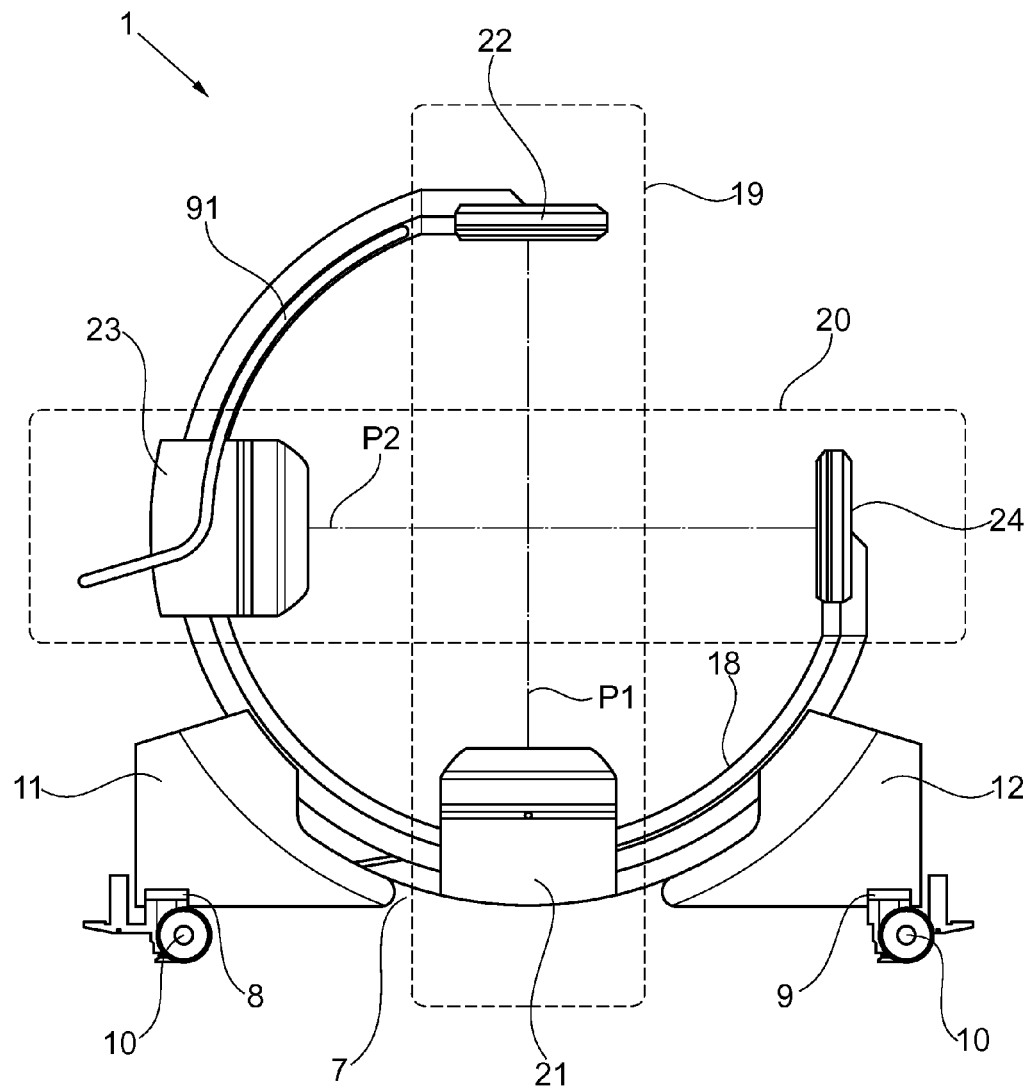

One embodiment of the apparatus shown in FIG. 1 to FIG. 5 comprises a mobile unit 1 provided with two X-ray systems 19, 20 mounted to operate and transmit X-ray beams along mutually intersecting axes P1, P2. The arm 18 of the embodiment illustrated in FIG. 1 is referred to as a G-arm.

An object, typically the body of a patient undergoing surgery, is placed inside the mobile unit 1 so that beam axis P1 and beam axis P2 of the two X-ray systems cross within the object. The first X-ray device 19 includes a first transmitter 21 (an X-ray tube or x-tube) for emitting X-rays and a first receiver 22 (e.g. image intensifier or flat screen semiconductor sensors) for receiving X-rays emitted by the first transmitter 21 and having passed through the object. The first transmitter 21 may be located down below on the arm 18 and the first receiver 22 at the top of the arm 18. The second X-ray device 20 includes a second transmitter 23 (an X-ray tube or x-tube) for emitting X-rays and a second receiver 24 (e.g. image intensifier or semiconductor sensors) for receiving X-rays emitted by the second transmitter 23 and having passed through said object. The receivers 22, 24 may each comprise image intensifying means and an image capturing device, typically a CCD camera, for converting X-rays into a visible image.

Figure 5:
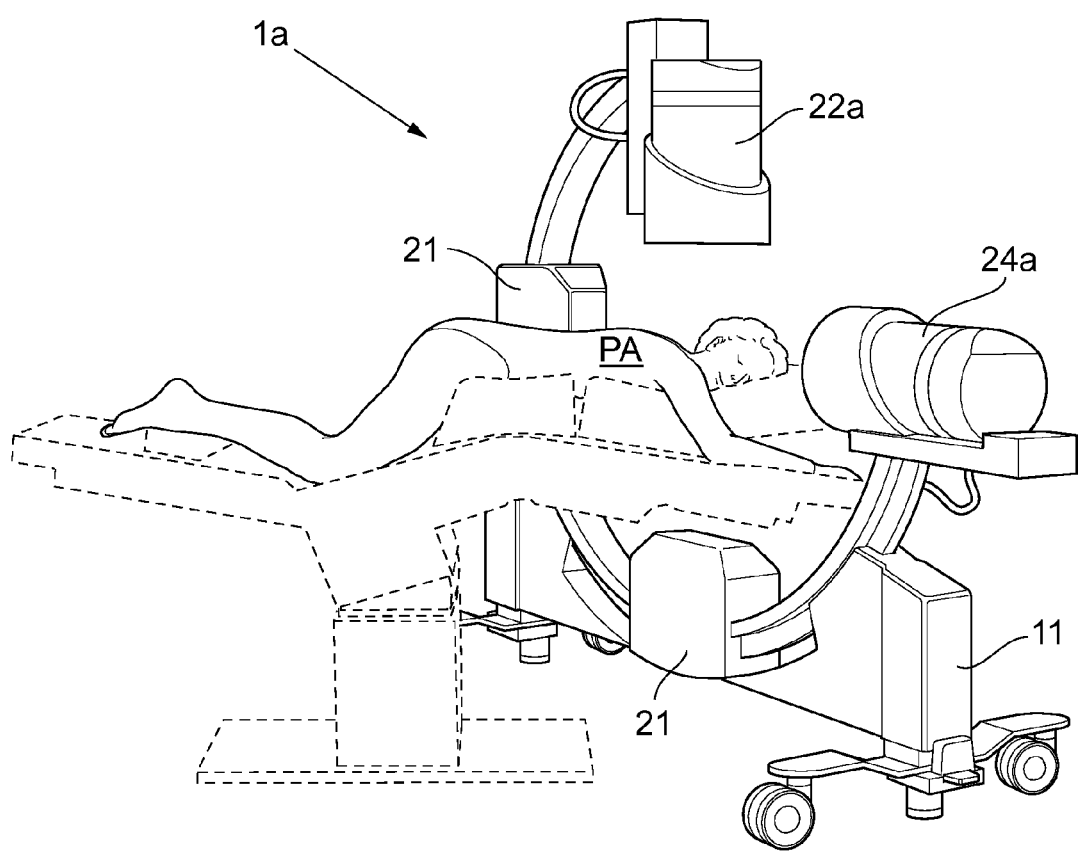

FIG. 5 shows the placement of an exemplary patient PA in a mobile fluoroscopy system. In this G-arm system shown in FIG. 5, the receivers 24a and 22a are traditional receivers and not flat screen receivers 22, 24 as shown in the G-arms of FIGS. 1-4.

Figure 6:
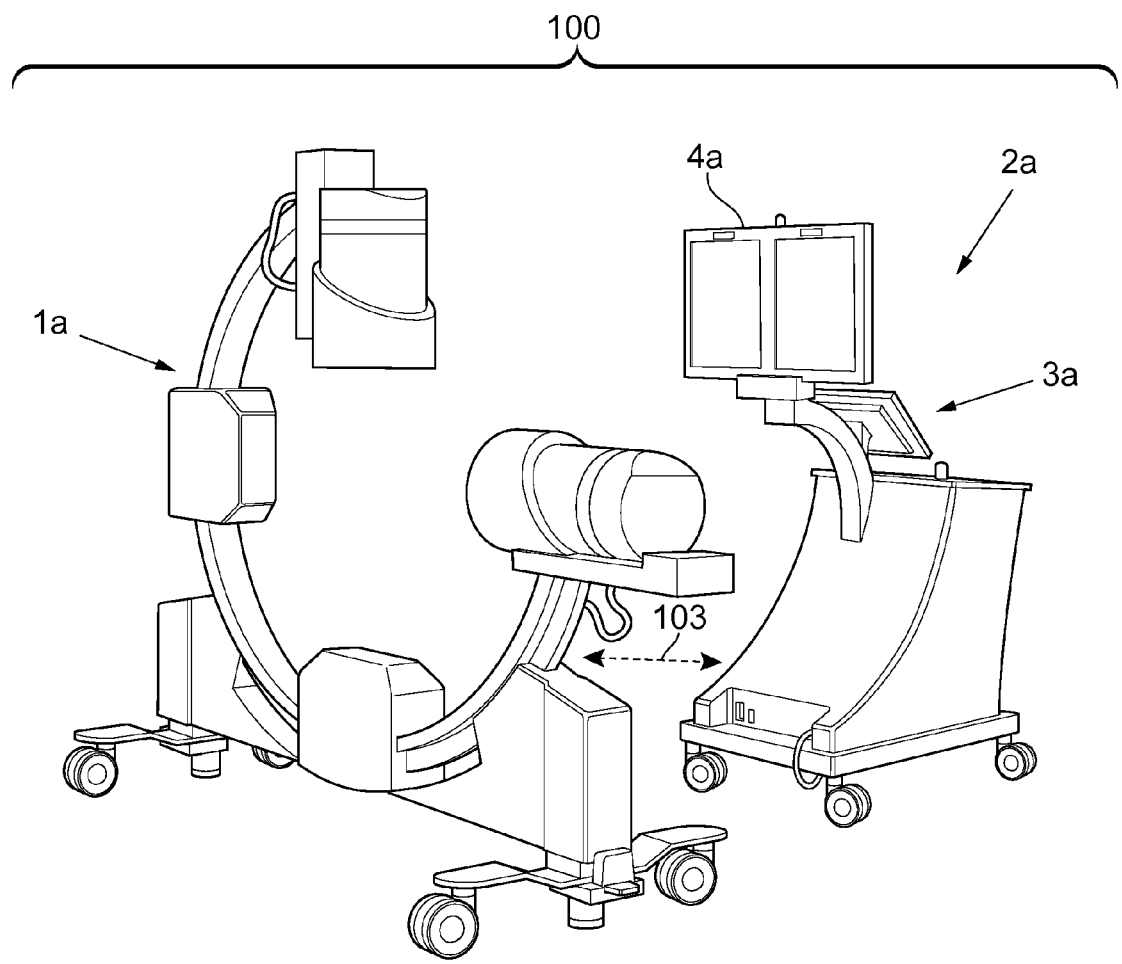

FIG. 6 shows a G-arm of the type shown in FIG. 5, to be placed around the patient as shown in FIG. 5 together with a separate console 2a which can be operated by the surgeon prior to the operation or during the operation by an assistant who does not have sterility restraints. High definition monitors 4a face the surgeon displaying the X-ray images in two different orthogonal planes either in real time or in so called "cine" replay to review exactly how and precisely where a prosthetic joint component has been placed without the necessity of exposing the patient and surgeon to more X-ray radiation.

Figure 7:
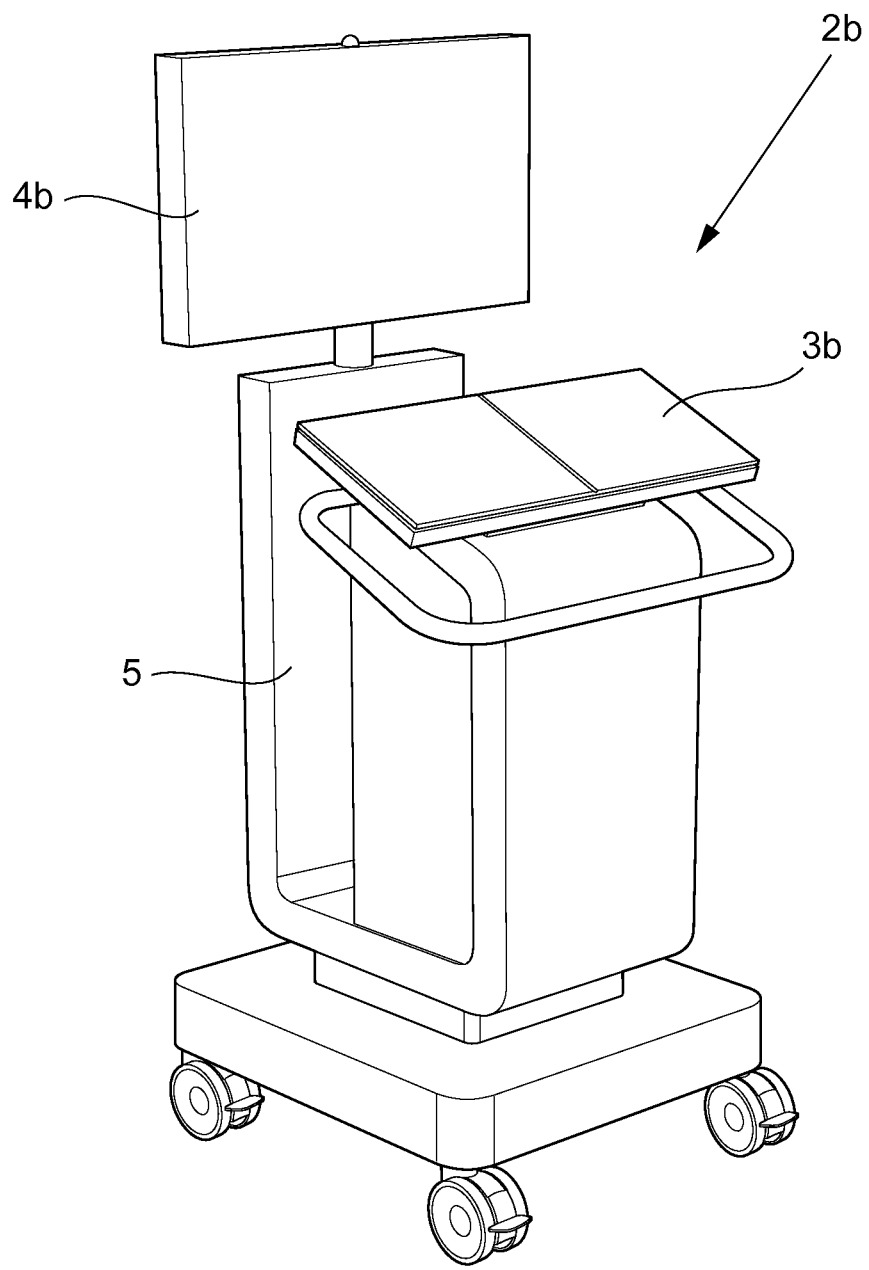
Figure 8A:
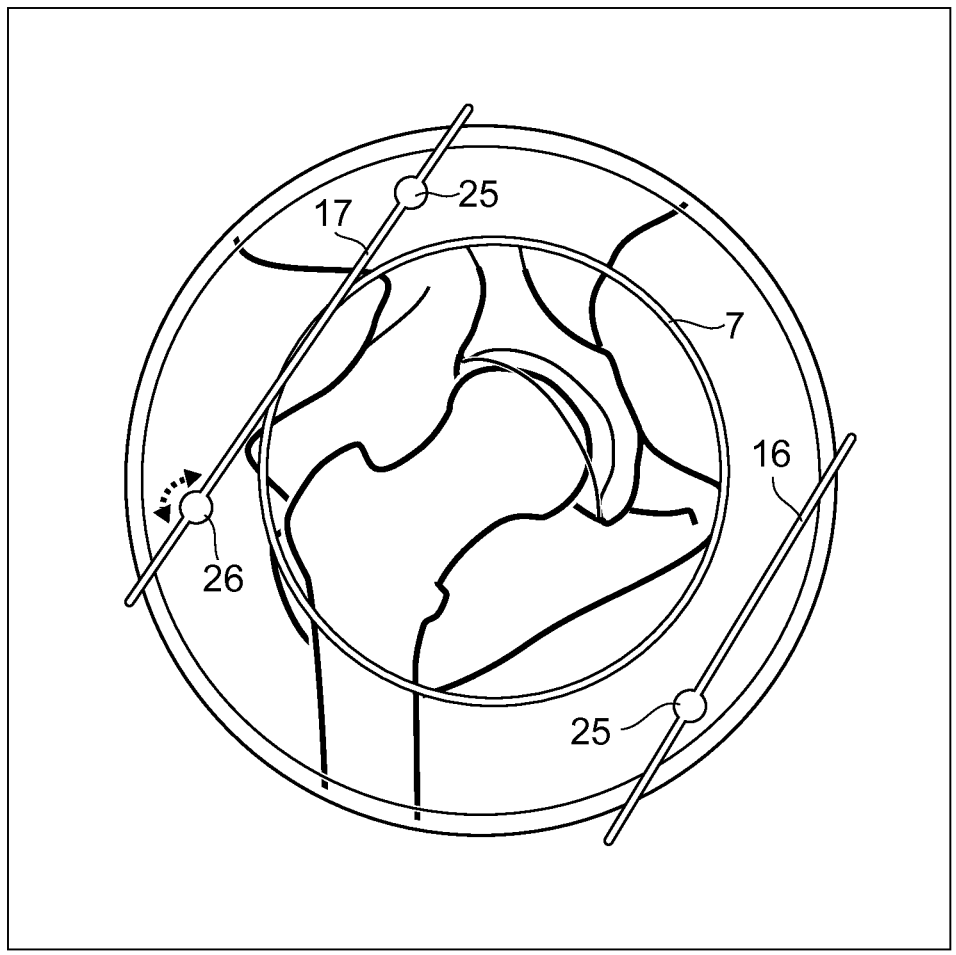
FIG. 8a shows a console view along one axis showing a collimator iris and two collimator plates represented overlaid on an X-ray image of a hip joint.
Figure 8B:
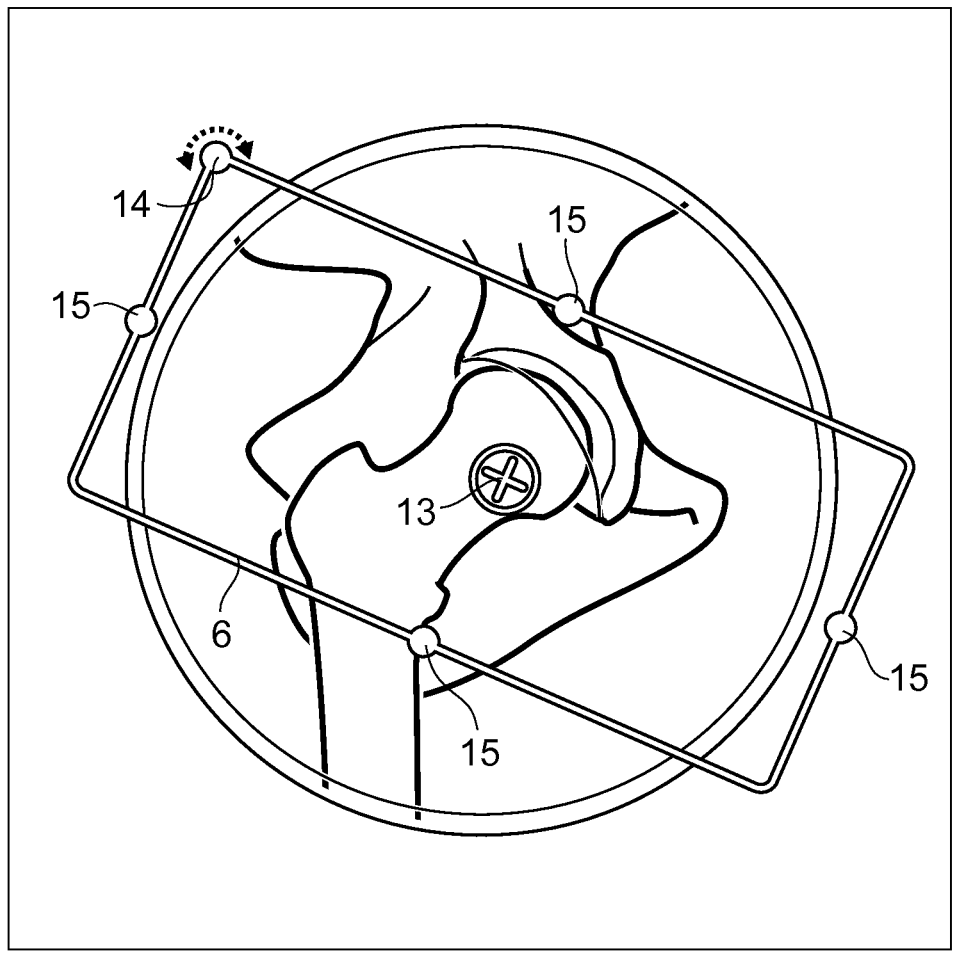
FIG. 8b shows a console view along one axis showing four collimator plates in a rectangle represented overlaid on an X-ray image of a hip joint.
Figure 9:
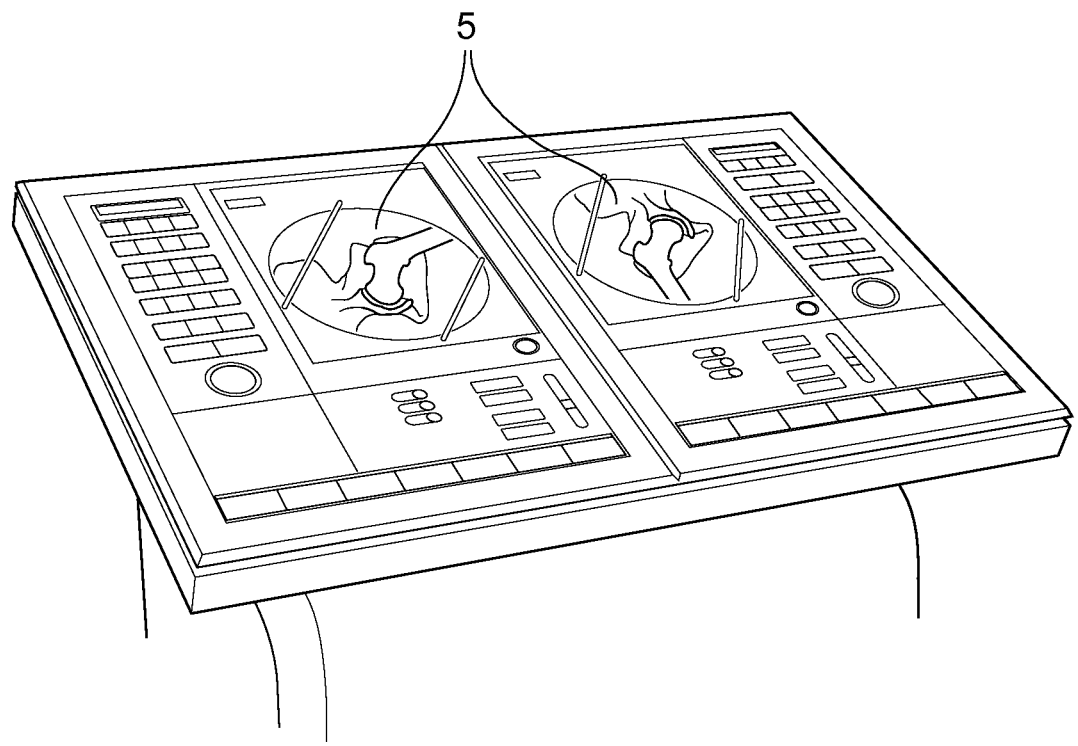
FIG. 9 shows a schematic view of a control unit in a console, with dedicated halves for the two axes of a G-stands, in a system according to the invention.
Figure 10:
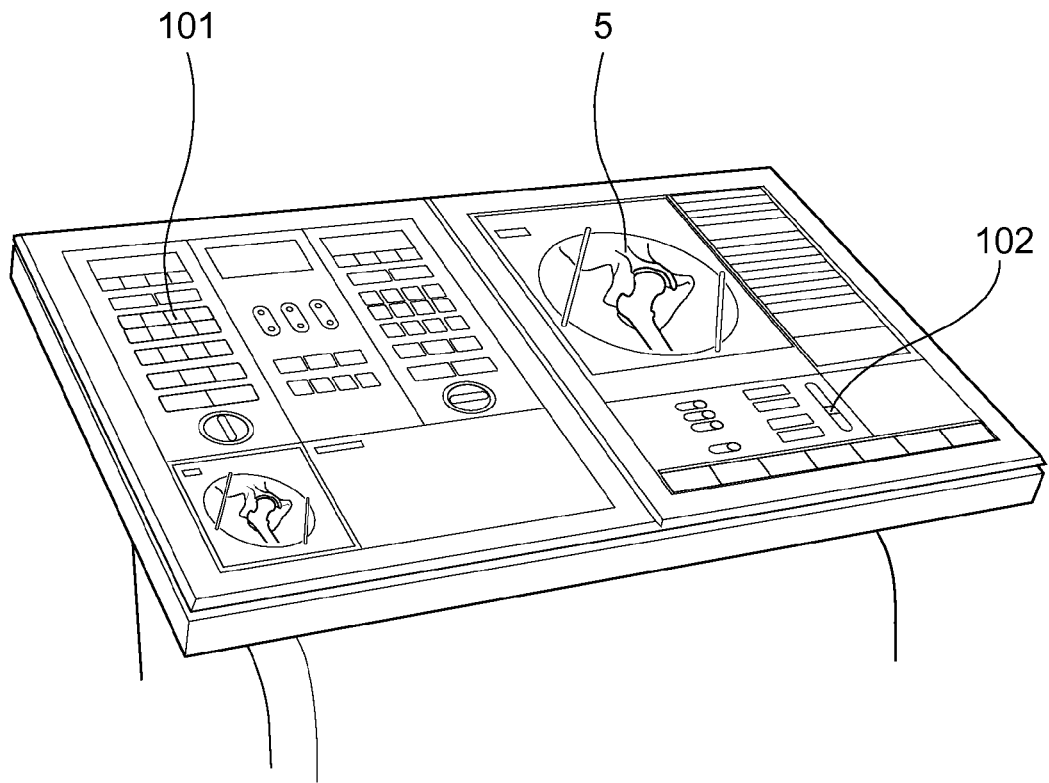
FIGS. 10 and 11 show schematic views of a control unit in a console with other configurations of the touchscreen.
Figure 11:
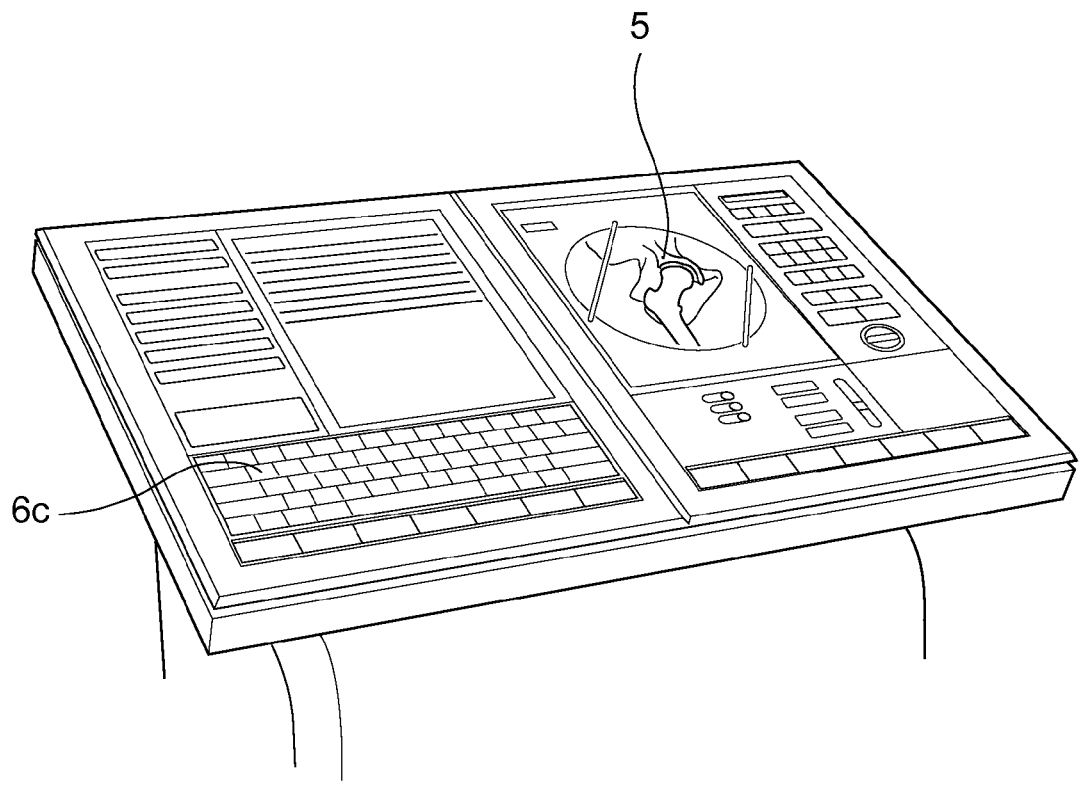

FIG. 7 shows another console 2b to be used in an X-ray system according to the invention. The HD display monitors 4b are shown here facing the operator of the console. During an operation, the high definition monitors will typically be turned around to present the fluoroscopic images to the surgeon. The cables connecting the G-stand to the console can be wound up and stored in the slot 5 when the console and the G-stand are close to each other. The console shown in FIG. 7 has a touch screen graphic user interface (GUI) 3b, comprising in this case two fields which can be configured in various ways as shown in FIGS. 9-11. FIG. 9 for example shows horizontal and vertical x-ray views 5 of a prosthesis mounted in a patient's hip, each view being surrounded by touch screen button 101 or slide 102 controls as well as numerical or analogue read-outs. FIG. 11 shows a configuration in which the left half of the touchscreen has a keyboard 6c for inputting and recording information to identify patient or operation information for example and "cine" recordings.

Each x-ray transmitter 21 and 23 is provided with a servo motor unit and servo motors moving collimator plates which must be adjusted to limit the exposed area of the patient to only the area of interest required to adequately perform the operation. Each transmitter is typically equipped with two pairs of collimator plates arranged perpendicularly to each other to form a rectangular exposure area 6 which must be adjusted to limit X-ray exposure. It is also possible to provide the mobile X-ray apparatus with servo motors moving a circular collimator iris.

Such a system may also comprise high resolution monitors or touch screens for presenting images to a surgeon for example and a user input unit, such as a foot switch (not shown) or touch screen functionality of the monitor to enable the surgeon with sterile hands to display X-ray images and control the area of interest. The system further comprises a control unit (2a, 2b) comprising at least one touch screen display for displaying image data, a control panel, and a data processor comprising image processing means adapted to receive images transmitted from said image capturing devices comprised in said receivers 22, 24. This is illustrated in FIG. 6, wherein a system comprises a mobile unit 1a and a control unit 2a. The mobile unit 1a and the control unit 2a are communicatively coupled to each other, for instance by means of a cable or through wireless signal transmission, which is indicated by the dashed arrow in FIG. 6.

The control unit is further configured to receive user indications via said touch screen as user input data in the form of user input data signals, to process user input data to control data indicative of a desired servo motor position, to send said control data as control signals to a servo motor unit, to receive servo motor status data as status control signals from a servo motor unit, to process servo motor status data to a visual representation of said servo motor status data and to send said visual representation to said touch screen as a display signal, wherein said touch screen is configured to display said visual representation to a user.

The control unit further comprises a processor/processing unit provided with specifically designed programming or program code portions configured to control the processing unit to perform the steps and functions of embodiments of the inventive method described herein. The control unit further comprises at least one memory configured to store data values or parameters received from a processor or to retrieve and send data values or parameters to a processor. The control unit further comprises a communications interface configured to send or receive data values or parameters to/from a processor to/from external units via the communications interface.

In one or more embodiments the processor/processing unit may be a processor such as a general or specific purpose processor/processing unit for example a microprocessor, microcontroller or other control logic that comprises sections of code or code portions, stored on a computer readable storage medium, such as a memory, that are fixed to perform certain tasks but also other alterable sections of code, stored on a computer readable storage medium, that can be altered during use. Such alterable sections of code can comprise parameters that are to be used as input for the various tasks, such as receiving user indications.

In one or more embodiments the control unit further comprises a display configured to receive a display signal from a processor and to display the received signal as a displayed image, e.g. to a user control.

In one or more embodiments the control unit further comprises an input device, e.g. integrated in the touch screen, configured to receive input or indications from a user as user input data.

In one or more embodiments, wherein communications interface may include at least one of a Local Area Network (LAN), Metropolitan Area Network (MAN), Global System for Mobile Network (GSM), Enhanced Data GSM Environment (EDGE), High Speed Downlink Packet Access (HS-DPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX), infrared communications and ultrasonic communication, etc., but is not limited thereto.

In one or more embodiments, the processor/processing unit is communicatively coupled and communicates with a memory where data and parameters are kept ready for use by the processing unit. The one or more memories may comprise a selection of a hard RAM, disk drive, a floppy disk drive, a magnetic tape drive, an optical disk drive, a CD or DVD drive (R or RW), or other removable or fixed media drive.

The system further comprise a servo motor unit configured or adapted to receive control data as control signals from said control unit, to control servo motors to a predetermined position based on said control data by sending servo motor signals, to obtain servo motor status data indicative of the status of a servo motor by receiving servo motor signals and to send servo motor status data as status control signals to said control unit. The servo motor unit and the servo motors are communicatively coupled to each other, for instance by means of a cable or through wireless signal transmission. The servo motor unit and the control unit 2a are communicatively coupled to each other, for instance by means of a cable or through wireless signal transmission.

In one embodiment a transmitter comprise a dedicated servo motor unit controlling servo motors moving collimator plates and/or a collimator iris narrowing the area of interest.

In one embodiment a common servo motor unit is shared by a first transmitter and a second transmitter, wherein the servo motor unit is controlling servo motors moving collimator plates and/or a collimator iris narrowing the area of interest for both the first and the second transmitter.

In non-limiting example, the servo motor status data is indicative of the position and/or if the servo motor is stationary or moving, i.e. has not yet reached a position corresponding to the a new irradiation area so that the transmitter can radiate the new irradiation area of interest.

The servo motor unit further comprises a processor/processing unit provided with specifically designed programming or program code portions configured to control the processing unit to perform the steps and functions of embodiments of the inventive method described herein. The servo motor unit further comprises at least one memory configured to store data values or parameters received from a processor or to retrieve and send data values or parameters to a processor. The servo motor unit further comprises a communications interface configured to send or receive data values or parameters to/from a processor to/from external units via the communications interface.

In one or more embodiments the processor/processing unit may be a processor such as a general or specific purpose processor/processing unit for example a microprocessor, microcontroller or other control logic that comprises sections of code or code portions, stored on a computer readable storage medium, such as a memory, that are fixed to perform certain tasks but also other alterable sections of code, stored on a computer readable storage medium, that can be altered during use. Such alterable sections of code can comprise parameters that are to be used as input for the various tasks, such as controlling servo motors.

In one or more embodiments, the servo motors control four straight collimator shutters forming a rectangle represented on the GUI touchscreen.

In one or more embodiments, the servo motors control the collimator iris and the two collimator shutters 1360 on either side of the iris.

In one or more embodiments, the servo motor unit further comprises one or a plurality of servo motors configured to receive servo motor signals from said processor and to move to a predetermined position, thereby moving a connected collimator or iris, and to indicate the status of said servo motor, such as the position or if the servo motor is stationary or moving, by sending servo motor signals to said processor.

In one or more embodiments, wherein communications interface may include at least one of a Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX), infrared communications and ultrasonic communication, etc., but is not limited thereto.

In one or more embodiments, the processor/processing unit is communicatively coupled and communicates with a memory where data and parameters are kept ready for use by the processing unit. The one or more memories may comprise a selection of a hard RAM, disk drive, a floppy disk drive, a magnetic tape drive, an optical disk drive, a CD or DVD drive (R or RW), or other removable or fixed media drive.

In one or more embodiments, the servo motor unit is comprised in a first transmitter and/or a second transmitter.

In one or more embodiments, the servo motor unit is comprised in the mobile unit separately from the first transmitter and/or the second transmitter.

Generally, in FIGS. 1-11 the following reference numbers refer to the listed parts of the fluoroscopy system, wherein any or all of the listed parts may be included according to different embodiments described herein:

1, 1a Mobile unit
2, 2a Control unit
7 Chassis frame
8, 9 Wheel units
10 Wheels
11, 12 Vertical columns, allowing vertical adjustments
13 Midpoint of collimator irradiation rectangle
14 Rotation corner
15 Mid-side movement point
16 Iris side collimator
17 Iris side collimator
25 Iris side collimator touch point
26 Iris side collimator rotation point
18 G-arm
19 First X-ray device 2
20 Second X-ray device
21 First transmitter
22 First receiver
23 Second transmitter
24 Second receiver
P1, P2 Intersecting axes
91 Handle
100 Fluoroscope system, or fluoroscopy system
120 Foot pedal unit holder
160 Cable holder

EMBODIMENTS AND FEATURES OF THE INVENTION

In one embodiment, four protective lead collimators or shutters, disposed at each transmitter, are arranged to form an area of interest or a rectangular space around the area to be irradiated. These four collimators for each transmitter can be moved, through servo motor mechanisms, by user indications, such as fingertip movement, on the touch screen of the control unit, wherein the current irradiated area is indicated as a rectangle. Usually this adjustment is performed when there is a previously acquired an x-ray still image on the screen. Such a rectangle is labeled 6 in FIG. 8. The rectangle appears as an overlay on the still image. The midpoint of the rectangle is indicated at 13. By touching this rectangle midpoint 6 with the fingertip, it is possible to move the rectangle translationally (resolution 1 mm), that is in any direction but preserving its orientation. While the midpoint 13 is used for translational movement of the rectangle, the corner point 14, is used to rotate (resolution 1°) the triangle about the corner point 14. To do this, the user merely touches the corner point 14 with his or her fingertip and twists it in the desired direction of rotation. Thus the rectangle can be turned to any orientation and placed at any location in the field of view.

The size of the rectangular exposed space can be adjusted by placing ones fingertip on one of the four circles 15 halfway along each side of the rectangle and moving it perpendicularly to the side. This perpendicular movement of the fingertip will narrow or broaden the rectangle 6 around the midpoint 13.

In one or more embodiments, an x-ray image and a user indicated irradiated area is displayed simultaneously on the touchscreen.

In one or more embodiments, user input is determined based on predetermined control points associated to the displayed irradiated area, wherein the control points are located on the perimeter or in the center of the overlaid irradiated area.

In one or more embodiments, the control points are one or more of:

An upper vertical control point configured to adjust the size of the irradiated area in the vertical direction An lower vertical control point configured to adjust the size of the irradiated area of interest in the vertical direction an upper horizontal control point configured to adjust the size of the irradiated area in the horizontal direction an lower horizontal control point configured to adjust the size of the irradiated area in the horizontal direction an offset control point configured to adjust the offset of the area of interest The control unit then receives a user indication of the rectangle as user input data, processes the user input data to control data, sends the control data to a servo motor unit configured or adapted to receive control data as control signals from said control unit, to control servo motors to a predetermined position.

Since each transmitter 21, 23 has its individual set of four collimators, the console is divided into two halves (see FIG. 9) each showing the area of interest from a vertical or horizontal perspective. Each collimator set of four shutters can be adjusted with ones fingertips, as a user indication, on its side of the screen as described above.

As an alternative, particularly when the system is equipped with one or more round image intensifiers instead of one or more flat screen detectors, the X-ray system according to the invention can have an IRIS collimator 7 instead. By touching the center point of the circle, which is fixed, the diameter of the circle can be changed. It is also provided with two parallel straight collimators, 16 and 17. It is possible to rotate the two straight collimators in parallel to each other by touching ones fingertip to the rotational point 14 and twisting, in the manner of manipulating the rectangle via corner point 14 as described above. The two straight side collimators 16 and 17 can be moved perpendicularly by touching the point 25 and moving it to one side or the other.

The control unit then receives a user indication of the diameter or rectangular area as user input data, processes the user input data to control data, sends said control data to a servo motor unit configured or adapted to receive control data as control signals from said control unit, to control servo motors to a predetermined position.

In one or more embodiments, the new irradiation area e.g. a rectangle or a diameter, is displayed on the touchscreen together with information indicative of whether the servo motors have completed their movement to the positions ordered by the control signals or are still it motion there.

In these two alternative touch screen collimator embodiments, there is always a slight delay after the user gives a user indication by moving the bars representing the collimator shutters on the touch screen until the servo motors controlling the physical collimator shutters have reached the positions corresponding to those indicated by a user on the touchscreen. During this delay time, the new area and/or current area of interest of interest is presented on the touchscreen together with information indicative of whether the servo motor is stationary or moving.

In one or more embodiments, the information indicative of if the servo motor is stationary or moving is indicated by the representational bars on the screen flash flashing and they then stop flashing when the actual physical collimator shutter reaches the position of the bar shown on the screen.

In one non-limiting example, a rectangle indicating the new irradiation area and or a rectangle indicating the current irradiation area of interest is/are presented as flashing objects on the touchscreen.

In one or more embodiments, a servo motor unit is configured to obtain servo motor status data indicative of the status of a servo motor by receiving servo motor signals and to send servo motor status data as status control signals to said control unit.

In one or more embodiments, a control unit is configured to receive servo motor status data as status control signals from a servo motor unit, to process servo motor status data to a visual representation of said servo motor status data and to send said visual representation to said touch screen as a display signal, wherein said touch screen is configured to display said visual representation to a user.

In one or more embodiments, the servo motor unit and the servo motors are communicatively coupled to each other, for instance by means of a cable or through wireless signal transmission.

In one or more embodiments, the servo motor unit and the control unit 2a are communicatively coupled to each other, for instance by means of a cable or through wireless signal transmission.

In one or more embodiments, a computer program product comprising computer readable code configured to, when executed in a processor, perform any or all of the method steps described herein.

In one or more embodiments, a non-transitory computer readable memory on which is stored computer readable code configured to, when executed in a processor, perform any or all of the method steps described herein.

A tangibly embodied computer-readable medium including executable code that, when executed, causes a control unit to perform any or all of the method steps described herein. A tangibly embodied computer-readable medium including executable code that, when executed, causes a servo motor unit to perform any or all of the method steps described herein.

The invention claimed is:

1. A mobile digital fluoroscopy system, comprising a mobile unit (1) having:
   a stand having an arm (18) suspended on a chassis frame (7);
   at least a first X-ray imaging device (19) mounted on the arm (18) to transmit and receive an X-ray beam along a first axis (P1), the first X-ray device (19) having a first receiver (22) mounted on the arm (18) and a first transmitter (21) mounted on the arm (18) opposite said first receiver (22) and a first set of adjustable collimator shutters disposed between the transmitter and the receiver;
   a console having an individual touchscreen for setting and operating said at least a first X-ray device, whereby said first set of collimator shutters are positionally adjustable by user input in the form of fingertip pressure and movement over a representation on the touchscreen of the collimator shutters overlaid on an X-ray image.

2. A mobile digital fluoroscopy system according to claim 1, comprising a mobile unit (1) having:
   a stand having a G-arm (18) suspended on a chassis frame (7);
   a first X-ray imaging device (19) mounted on the G-arm (18) to transmit and receive an X-ray beam along a first axis (P1), the first X-ray device (19) having a first receiver (22) mounted on the G-arm (18) and a first transmitter (21) mounted on the G-arm (18) opposite said first receiver (22) and a first set of adjustable collimator shutters disposed between the transmitter and the receiver;

a second X-ray imaging device (20) mounted on the G-arm (18) to transmit and receive an X-ray beam along a second axis (P2) intersecting the first axis (P1) of the first X-ray device, the second X-ray device (20) having a second receiver (24) mounted on the G-arm (18) and a second transmitter (23) mounted on the arm (18) opposite said second receiver (24) and a second set of adjustable collimator shutters disposed between the transmitter and the receiver, a console having an individual touchscreen for setting and operating each of said first and second X-ray devices, whereby said first and second sets of collimator shutters are positionally adjustable by user input in the form of fingertip pressure and movement over a representation on the touchscreen of the collimator shutters overlaid on an X-ray image.

3. A mobile digital fluoroscopy system according to claim 1 or 2, wherein each of said X-ray receivers is a tubular image intensifier.

4. Mobile digital fluoroscopy system according to claim 1 or 2, wherein each of said X-ray receivers is a flat screen receiver.

5. Mobile digital fluoroscopy system according to claim 1 or 2, wherein said touchscreen representation of the collimator shutters is presented in the form of a rectangle composed of four sides.

6. Mobile digital fluoroscopy system according to claim 1 or 2, wherein said touchscreen representation of the collimator shutters is presented in the form of a circle and two side lines.

7. Mobile digital fluoroscopy system according to claim 5, wherein the symmetrical center point of said rectangle is a fingertip touch point, whereby touching said rectangle center point and moving a fingertip in contact with the touchscreen moves the rectangle translationally in a corresponding manner across the X-ray image.

8. Mobile digital fluoroscopy system according to claim 5 or 7, wherein each side in said rectangle has a fingertip touch point whereby said side can be moved laterally to symmetrically narrow or widen said rectangle, or alternatively symmetrically lengthen or shorten said rectangle and thereby effect a corresponding locational readjustment of the four collimator shutters.

9. Mobile digital fluoroscopy system according to claim 5, 7 or 8, wherein said rectangle has a fingertip touch point at one corner whereby said rectangle, by twisting the fingertip in contact with the corner touch point can rotate said rectangle around said corner touch point in relation to said X-ray image, and thereby effect a corresponding locational readjustment of the four collimator shutters.

10. Mobile digital fluoroscopy system according to claim 6, wherein the center point of the representational circle is a fingertip touch point whereby fingertip pressure adjusts the diameter of the circle overlaid on the X-ray image and effects a corresponding physical enlargement or shrinking of a collimator iris.

11. Mobile digital fluoroscopy system according to claim 6, wherein each of the two side lines has a fingertip touch point whereby each side can be moved laterally in parallel to the other of the two side lines.

12. Mobile digital fluoroscopy system according to claim 6, wherein one of the two side lines has a fingertip touch point whereby twisting the fingertip in contact with the rotational touch point (26) rotates both side lines in parallel about said rotational touch point and effects a corresponding locational readjustment of the two straight collimator shutters.

13. Mobile digital fluoroscopy system according to one of the preceding claims, wherein said system is provided with servo motors associated with each adjustable collimator, said servo motors being disposed to effect adjustment of the collimators in response to touchscreen fingertip commands.

14. Mobile digital fluoroscopy system according to claim 13, wherein said servo motors, when in operation, provide a signal to said touchscreen, which displays an indication to the user that the servomotor is still in operation and that the collimator has not yet reached its destination ordered by the touchscreen fingertip commands.

15. A method in a console having an individual touchscreen, said console having an individual touchscreen for setting and operating said at least a first X-ray device, whereby a first set of collimator shutters are positionally adjustable by user input in the form of fingertip pressure and movement over a representation on the touchscreen of the collimator shutters overlaid on an X-ray image.

16. A computer program product comprising computer readable code configured to, when executed in a processor, perform any or all of the steps of the method in claim 15.

17. A non-transitory computer readable memory on which is stored computer readable code configured to, when executed in a processor, perform any or all of the steps of the method in claim 15.

* * * * *